(12) United States Patent
Enomoto (10) Patent No.: US 7,822,178 B2
(45) Date of Patent: Oct. 26, 2010

(54) RADIOGRAPHIC IMAGING SYSTEM

(75) Inventor: Jun Enomoto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/461,460

(22) Filed: Aug. 12, 2009

(65) Prior Publication Data
US 2010/0040199 A1 Feb. 18, 2010

(30) Foreign Application Priority Data
Aug. 13, 2008 (JP) .............................. 2008-208629

(51) Int. Cl.
*H05G 1/08* (2006.01)
(52) U.S. Cl. ........................................ 378/91; 378/207
(58) Field of Classification Search .................... 378/91, 378/94, 95, 97, 98, 98.4, 98.11, 98.12, 207; 382/130–133
See application file for complete search history.

(56) References Cited

U.S. PATENT DOCUMENTS

2003/0223539 A1* 12/2003 Granfors et al. ............ 378/98.8
2004/0258201 A1* 12/2004 Hayashida .................... 378/62
2010/0020933 A1* 1/2010 Topfer et al. ............. 378/98.11

FOREIGN PATENT DOCUMENTS

JP 2005-283422 10/2005

\* cited by examiner

*Primary Examiner*—Hoon Song
(74) *Attorney, Agent, or Firm*—Jean C. Edwards, Esq.; Akerman Senterfitt (57) ABSTRACT

A radiographic imaging system comprises: offset correction unit for performing offset correction on a radiographic image acquired by a radiation detector using a offset correction data in a storage, dark image acquisition unit for acquiring a dark image with the radiation detector at a given timing in the absence of radiation emitted from a radiation source, residual image judgment unit for judging whether or not dark image acquired by the dark image acquisition unit contains a residual image resulting from an immediately preceding irradiation, offset correction data renewal unit for producing offset correction data based upon the dark image and storing the offset correction data in the storage for renewal when the residual image judgment unit judges the dark image to contain no residual image, and producing no offset correction data when the residual image judgment unit judges the dark image to contain a residual image.

10 Claims, 5 Drawing Sheets

RADIOGRAPHIC IMAGING SYSTEM

CROSS-REFERENCE TO RELATED APPLICATIONS

The present application claims priority from Japanese Patent Application No. 2008-208629, filed Aug. 13, 2008, the contents of which are herein incorporated by reference in their entirety.

BACKGROUND OF THE INVENTION

The present invention relates to a radiographic imaging system whereby a subject is irradiated with radiation and whereby the radiation that has penetrated the subject is detected by a radiation detector and converted into an electric signal to produce a radiographic image based upon the electric signal obtained by the conversion. The present invention relates in particular to a radiographic imaging system having a function of correcting the offset of data in the radiation detector.

Radiographic imaging systems are used in a variety of fields such as medicine where they are used to produce diagnostic images for medical use and industries where they are used to conduct nondestructive tests. Presently, some radiographic imaging systems use a flat panel detector (FPD), which converts radiation into an electric signal, as a radiation detector for detecting the radiation that has penetrated a subject (e.g., X-ray, α ray, β ray, γ ray, electron beam, and ultraviolet ray).

There are two types of methods that use an FPD as a radiation detector: a direct type and an indirect type. The method of the direct type, for example, collects electron-hole pairs (e-h pairs) generated by a photoconductive film such as one formed of amorphous selenium in response to incident radiation and reads out them as an electric signal. To be brief, the direct type directly converts radiation into an electric signal. The indirect type has a phosphor layer (a scintillator layer) formed of a phosphor that fluoresces in response to incident radiation to convert radiation into visible light through that phosphor layer, reading out the visible light with a photoelectric transducer. Briefly, the indirect type converts radiation into visible light and then converts the visible light into an electric signal.

In a radiographic imaging system using such an FPD, the pixels (radiation detection elements) of the FPD are producing a given electric signal (dark output) even when the FPD is not irradiated. The dark output is not necessarily the same among the pixels. Different pixels generate different dark output. Accordingly, a radiographic image obtained using such an FPD is affected by dark output (offset) from each pixel. Offset correction is an image processing performed to remove such an effect.

In one example of offset correction, an image (dark image) is read out from the FPD when it is not irradiated, and the dark image thus obtained is used as offset correction data, alternatively, necessary processing is performed on this dark image to produce offset correction data, whereupon the offset correction data is subtracted from a radiographic image as taken.

The offset of the FPD changes with time due to the temperature variation and other factors. Thus, it is a known practice to renew the offset correction data at a given timing.

JP 2005-283422 A, for example, describes a radiographic imaging system comprising offset correction data registering means for registering offset correction data acquired according to an offset signal read out as correction data from radiation detecting means when it is not irradiated, offset correction data renewal means for renewing the offset correction data registered in the offset correction data registering means by using an offset signal, irradiation/non-irradiation detecting means for detecting irradiation and non-irradiation, and data processing switching means. In this radiographic imaging system, when non-irradiation is detected by the irradiation/non-irradiation detecting means, the data processing switching means causes the offset correction data renewal means to perform renewal processing. And, when irradiation is detected by the irradiation/non-irradiation detecting means while the offset correction data renewal means is performing renewal processing, the data processing switching means causes the offset correction data renewal means to stop the renewal processing, whereupon the data processing switching means causes correction computation means to perform correction processing. Afterward, when the irradiation/non-irradiation detecting means detects non-irradiation again, the data processing switching means causes the offset correction data renewal means to resume the interrupted renewal processing.

As described above, the offset of the FPD changes with time due to the temperature variation and other factors. To perform an appropriate offset correction, therefore, the offset correction data needs to be renewed as appropriate.

Renewal of offset correction data as described above is performed at a given timing, typically each time, for example, a given time elapses (at given intervals) or when the temperature of the radiographic imaging system (or the environment in which it is installed) undergoes a variation exceeding a given value.

Needless to say, the radiographic imaging system also carries out radiographic imaging while renewing offset correction data.

As is known, after radiographic imaging, and, in particular, after radiographic imaging using a great dose of radiation, an electric charge or a so-called residual image remains inside the FPD based on irradiation even after an image is read out. Although a residual image decreases over time, when radiographic imaging is performed with a residual image, the residual image is superimposed upon a radiographic image subsequently taken, making acquisition of an appropriate radiographic image impossible.

As described above, offset correction data is produced using the dark image in the FPD. When the dark image is read out with a residual image left in the FPD, the residual image is superimposed upon the dark image, making it impossible to produce appropriate offset correction data. When offset correction data affected by a residual image is used, an appropriate offset correction cannot be achieved, causing a quality degradation of the radiographic image.

SUMMARY OF THE INVENTION

It is an object of the invention to solve the above problems associated with the prior art and to provide a radiographic imaging system capable of producing a high image quality radiographic image by performing an offset correction free from a residual image.

A radiographic imaging system according to the present invention comprising:
 a radiation source for irradiating a subject with radiation,
 a radiation detector for detecting radiation that has penetrated the subject to acquire a radiographic image,
 a storage for storing offset correction data,
 offset correction means for performing offset correction on a radiographic image acquired by the radiation detector using the offset correction data in the storage, dark image acquisition means for acquiring a dark image with the radiation detector at a given timing in the absence of radiation emitted from the radiation source, residual image judgment means for judging whether or not a dark image acquired by the dark image acquisition means contains a residual image resulting from an immediately preceding irradiation, offset correction data renewal means for producing offset correction data based upon the dark image and storing the offset correction data in the storage for renewal when the residual image judgment means judges the dark image to contain no residual image, and producing no offset correction data when the residual image judgment means judges the dark image to contain a residual image.

A radiographic imaging system according to the present invention comprising:

a radiation source for irradiating a subject with radiation, a radiation detector for detecting radiation that has penetrated the subject to acquire a radiographic image, a storage for storing offset correction data, offset correction means for performing offset correction on the radiographic image acquired by the radiation detector using the offset correction data in the storage, dark image acquisition means for acquiring a dark image with the radiation detector at a given timing in the absence of radiation emitted from the radiation source, elapsed time judgment means for judging whether or not a given time period has elapsed after the radiation source has performed irradiation with a dose of radiation exceeding a given threshold.

offset correction data renewal means for producing offset correction data based upon the dark image and storing the offset correction data in the storage for renewal when the elapsed time judgment means judges that the given time period has elapsed, and producing no offset correction data when the elapsed time judgment means judges that the given time period has not elapsed.

DETAILED DESCRIPTION OF THE INVENTION

First Embodiment

Figure 1:
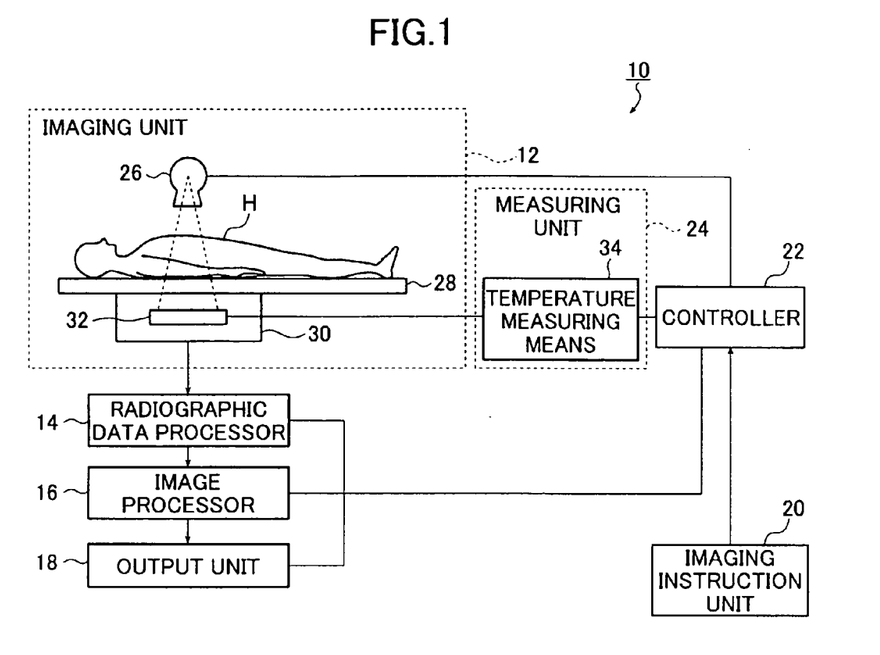
FIG. 1 is a conceptual view illustrating a configuration of a radiographic imaging system according to a first embodiment of the invention.

FIG. 1 is a conceptual view illustrating a configuration of the radiographic imaging system 10 according to the first embodiment of the invention. A radiographic imaging system (hereinafter referred to also as imaging system) 10 irradiates a test subject (examinee) H with radiation, and uses a radiation detector (flat panel detector, referred to as FPD below) 32 described later to detect and convert the radiation that has penetrated the test subject H into an electric signal corresponding to image data, thereby to obtain a radiographic image of the test subject H based upon this electric signal obtained by conversion.

The imaging system 10 comprises an imaging unit 12, a radiograph data processor 14, an image processor 16, an output unit 18, an imaging instruction unit 20, a controller 22, and a measuring unit 24.

The imaging unit 12 comprises a radiation source 26, an imaging table 28 upon which the subject H lies in a given position for imaging, and a radiation detector 30 for detecting the radiation that has penetrated the subject H.

In the imaging unit 12, the irradiation source 26 emits radiation, and the FPD 32 of the radiation detector 30 detects the radiation that has penetrated the subject H on the imaging table 28 to take a radiographic image of the subject H. The imaging unit 12 outputs data (analog data) of a radiographic image of the subject H.

The radiation source 26 may be any known radiation source used in various radiographic imaging systems.

The FPD 32 detects and converts the radiation that has penetrated the subject H into an electric signal to output radiographic image data (analog data) representing the subject H. The FPD 32 may be a known FPD, which, specifically, may be a direct type FPD whereby radiation is directly converted into an electric charge or an indirect type FPD whereby radiation is temporarily converted into light, which is then converted into an electric signal.

The direct type FPD is configured, for example, of a photoconductive film such as one made of amorphous selenium, capacitors, TFTs (thin-film transistor) as switching devices, and the like. Upon entry of radiation such as X-ray in the photoconductive film, for example, electron-hole pairs (e-h pairs) are emitted from the photoconductive film. The electron-hole pairs are stored in each capacitor, and the electric charge stored in the capacitor is read out through the corresponding TFT as an electric signal.

On the other hand, the indirect type FPD is configured, for example, of a scintillator layer formed of a phosphor, photodiodes, capacitors, TFTs, and the like. The scintillator layer is formed, for example, of a phosphor such as "CsI:T1" that emits light or fluoresces in response to incident light such as radiation. The light produced by the scintillator layer in response to incoming radiation undergoes photoelectric conversion through each photodiode to produce an electric charge, which is stored in the corresponding capacitor, and the electric charge stored in the capacitor is read out through the corresponding TFT as an electric signal.

The radiation source 26 and the radiation detector 30 may be so configured as to be capable of reciprocating along the length of the radiographic table 28 (leftwards and rightwards in FIG. 1) to enable, for example, long region imaging. Alternatively, the imaging table 28 may be movably provided.

The measuring unit 24 comprises temperature measuring means 34. The temperature measuring means 34 measures the temperature of the FPD 32 and supplies the measurement result to the controller 22.

The temperature measuring means 34 may be any of various known temperature measuring devices including contact type measuring devices exemplified by a thermocouple, a thermistor, etc., and non-contact type measuring devices such as a radiation thermometer.

The radiographic data processor 14 reads out image data from the imaging unit 12 (FPD 32) in response to an instruction from the controller 22 and performs given data processing such as analog-to-digital conversion on the read-out image data. The radiographic data processor 14 outputs data-processed image data (digital data).

The radiographic data processor 14 reads out image data from the FPD 32 basically according to an accumulation time. The accumulation time is a time during which radiation is converted into an electric charge and the electric charge is accumulated in the FPD 32.

In radiographic imaging of the subject H, for example, the radiographic data processor 14 reads out a radiographic image (radiographic image data) from the FPD 32 after a given accumulation time has elapsed from irradiation. The radiographic data processor 14 performs idle read at given accumulation time intervals in order to reduce the residual image amount (residual image) during a period from when a radiographic image is read out until the next radiographic image or a dark image is read out.

The radiographic data processor 14 reads out dark image for renewing offset correction data from the FPD 32 at given intervals and in response to an instruction from the controller 22 when the FPD 32 has undergone a variation in temperature exceeding a given threshold. This will be described later in detail.

The image data read out by the radiographic data processor 14 is subsequently transmitted to the image processor 16.

Figure 2:
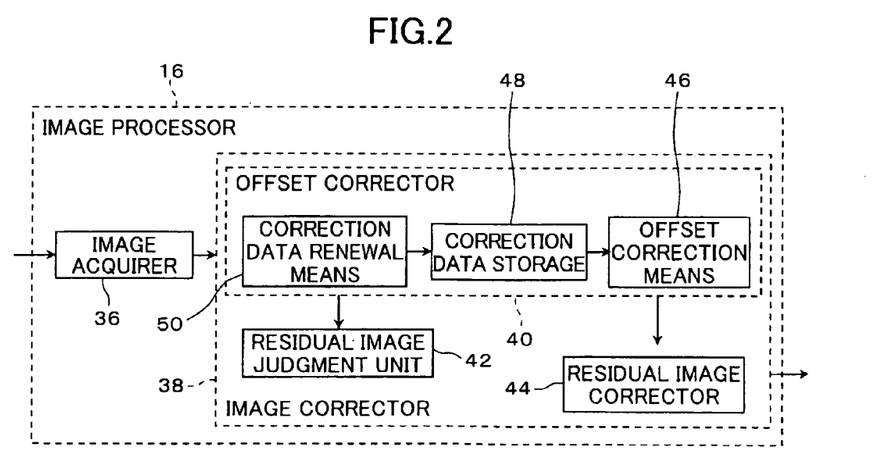
FIG. 2 is a block diagram illustrating a configuration of an image processor in the first embodiment.

As illustrated in FIG. 2, the image processor 16 comprises an image acquirer 36 and an image corrector 38 and performs given image processing such as offset correction and residual image correction on the image data acquired from the radiographic data processor 14. The image processor 16 outputs an image-processed radiographic image.

The image processor 16 is configured using a program (software) that runs in a computer or dedicated hardware or a combination of both.

The image acquirer 36 acquires the image data processed by the radiographic data processor 14 and transmits such image data to relevant units.

The image corrector 38 performs given image processing on the image data (radiographic image) acquired by the image acquirer 36.

In FIG. 2, the image corrector 38 performs offset correction and residual image correction on image data and comprises an offset corrector 40 and a residual image corrector 44. The image corrector 38 comprises a residual image judgment unit 42 to determine whether or not there remains a residual image from the previous imaging in the dark image acquired for renewal of the offset correction data (whether or not such a residual image is superimposed on the dark image).

The image processing by the image corrector 38 is not limited to offset correction and residual image correction but may also comprise all of various other image processing (image correction) including gain correction, sharpness processing, and tone correction as performed by known radiographic imaging systems.

The pixels (radiation detection elements) of the FPD 32 are producing a given electric signal (dark output) even when the FPD is not irradiated (dark mode). Such dark output is not necessarily the same among all the pixels. Different pixels produce different dark output. Accordingly, a radiographic image obtained using such an FPD is affected by dark output (offset) from each pixel (offset), i.e., an image having a degraded image quality.

The offset corrector 40 performs correction for preventing image degradation caused by such offset in the FPD 32 and comprises offset correction means 46, a correction data storage 48 for storing offset correction data that is used for offset correction, correction data renewal means 50 for renewing offset correction data.

The image acquirer 36 supplies a radiographic image to the offset correction means 46 and a dark image to the correction data renewal means 50, respectively.

The offset correction means 46 reads out offset correction data registered in the correction data storage 48, subtracts this offset correction data from the image data (radiographic image data) to perform offset correction on the image data, and supplies the corrected image data to the residual image corrector 44.

The present invention is not limited specifically in the method of offset correction but permits use of any known method using offset correction data produced from a dark image.

The correction data renewal means 50 supplies the supplied dark image to the residual image judgment unit 42.

The correction data renewal means 50 produces offset correction data using the dark image acquired by the image acquirer 36 from the image data processor 14 and registers the thus produced offset correction data in the correction data storage 48 as new offset correction data thereby to renew the offset correction data.

The correction data storage 48 registers (stores) offset correction data supplied from the correction data renewal means 50.

In the first embodiment, the dark image acquired from the FPD 32 and processed by the image data processor 14 for renewal of offset correction data is used as it is as new offset correction data.

However, the method of producing offset correction data is not limited to the above examples, and may be any of various offset correction data renewal methods known in the art including a method whereby, for example, an average of preliminarily stored offset correction data and an acquired dark image is obtained to use the average data as offset correction data, and a method whereby average data of successively acquired dark images is used as offset correction data.

The imaging system 10 according to the first embodiment renews offset correction data at given intervals and when the FPD 32 has undergone a variation in temperature exceeding a given threshold. The data renewal in the imaging system 10 may be achieved by any method including but not limited to a method whereby offset correction data is normally renewed at given intervals and additionally renewed between such time intervals in a case where a variation in temperature exceeding a given threshold has occurred.

When the FPD 32 has undergone a variation in temperature exceeding a given threshold has occurred and therefore offset correction data has been renewed, one may reset the time to resume counting the data renewal intervals from that reset time.

In the imaging system 10, the residual image judgment unit 42 determines whether or not the dark image acquired for offset correction data renewal contains a residual image. Only in the absence of residual image, the correction data renewal means 50 produces offset correction data using the dark image. The offset correction data thus produced is registered in the correction data storage 48 as renewed offset correction data. In other words, when the dark image acquired for offset correction data renewal contains a residual image, the offset correction data is not renewed.

The residual image judgment unit 42 analyzes the dark image supplied from the correction data renewal means 50 to determine the presence or absence of a residual image.

When supplied with a dark image from the correction data renewal means 50, the residual image judgment unit 42 calculates the pixel values of the respective pixels of the dark image. When a pixel among them has a pixel value exceeding a given threshold, the dark image is judged to contain a residual image; when all the pixels has a pixel value under the given threshold, the dark image is judged not to contain any residual image.

The residual image judgment unit 42 supplies the judgment result (a signal representing the result) as to the presence and absence of the residual image on the dark image to the correction data renewal means 50.

The pixel value used as a threshold for judgment as to the presence and absence of the residual image on the dark image is not limited specifically and may be set as appropriate according to, for example, the image quality required of the imaging system 10 and the frequency with which the offset correction data is renewed. Further, the threshold may be set for each imaging menu, each imaging condition, and the like or varied (adjusted) according to the imaging menu, imaging conditions, and the like.

The residual image judgment may be made not only by the above method but by any of other known methods as well including but not limited to a method whereby an average of the pixel values of all the pixels in an image is calculated to make a judgment based on the threshold, or a method whereby a "passed-through" area in an image resulting from radiographic imaging of a subject is used to judge a pixel value.

The residual image judgment unit 42 acquires a dark image from the correction data renewal means 50, makes residual image judgment on the dark image, and outputs the judgment result as to the residual image on the dark image to the controller 22. The invention is not limited thereto, however. For example, after a dark image is acquired from the image acquirer 36 to make residual image judgment, the dark image may be supplied to the correction data renewal means 50 only in the absence of residual image.

Now, the offset correction data renewal method will be described.

Figure 8:
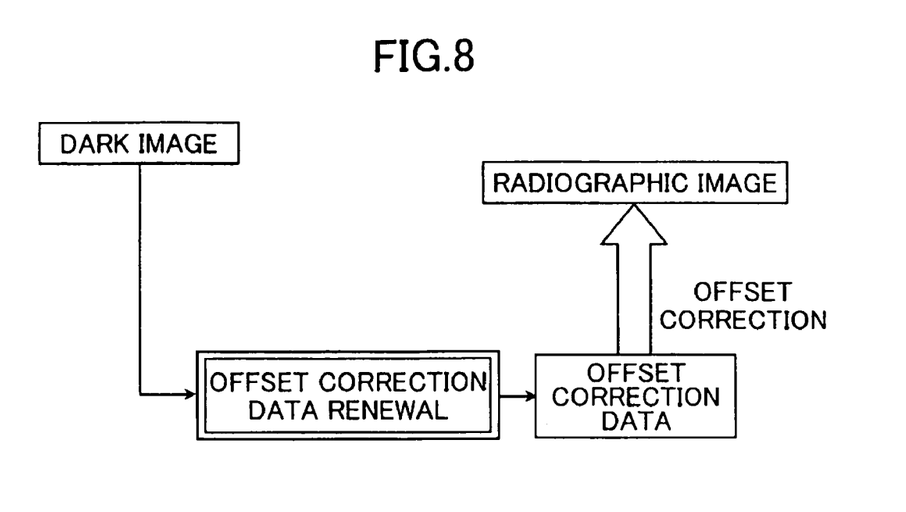
FIG. 8 is a view for explaining the operations of offset correction data renewal in a conventional radiographic imaging system.

The operations of the offset correction data renewal processing performed by a conventional radiographic imaging system illustrated in FIG. 8 will be described first.

In the conventional radiographic imaging system, a dark image is acquired from the FPD and used to renew offset correction data at a given timing during the time period from the startup of the system until the system is switched off. Where the renewal is effected as above, when a great dose of irradiation precedes acquisition of a dark image, for example, the dark image acquired under such a condition contains a residual image. Therefore, when offset correction is performed on the radiographic image using offset correction data that is in turn renewed using such a dark image, appropriate correction cannot be achieved, and the image quality of the radiographic image is degraded.

In contrast, in the first embodiment, judgment is made as to the presence and absence of a residual image on the dark image acquired for offset correction data renewal, and the offset correction data is renewed depending upon the judgment result.

Figure 3:
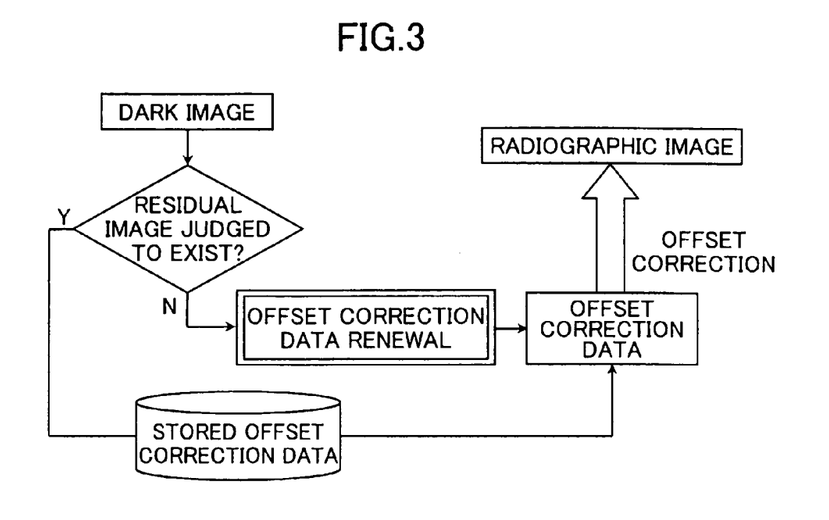
FIG. 3 is a view for explaining the operations of offset correction data renewal in the first embodiment.

Now, the operations of the offset correction data renewal processing performed by the first embodiment will be described referring to FIG. 3.

In the radiographic imaging system 10 according to the first embodiment, the radiographic data processor 14 acquires a dark image for renewing offset correction data from the FPD 32 at given intervals from the startup of the system until the system is switched off and when the FPD 32 has undergone a variation in temperature exceeding a given threshold. The acquired dark image is judged by the residual image judgment unit 42 for a residual image. When a judgment is made that there is no residual image (N), the correction data renewal means 50 renews offset correction data using the dark image judged to have no residual image.

In contrast, when the residual image judgment unit 42 judges that the dark image acquired for offset correction data renewal contains a residual image (Y), the offset correction data is not renewed. Accordingly, when a radiographic image is subsequently taken, offset correction is made on that radiographic image using the offset correction data which has been already stored in the correction data storage 48.

In the first embodiment, a judgment is made as to the presence and absence of a residual image on an acquired dark image, and the offset correction data is renewed only when a judgment is made that there is no residual image, making it possible to perform a consistently appropriate offset correction and obtain a high quality radiographic image.

When offset correction data is not renewed, not only may the offset correction data in storage be used for offset correction but offset correction data acquired in a calibration that is made at the startup of the system may also be used. More specifically, when the offset correction data has not been renewed for a long time although judgments verifying the presence of a residual image have been successively made and the offset correction data in storage is judged to be inappropriate, the offset correction data acquired in a calibration may be used for offset correction.

In the first embodiment, it is preferable to stop renewing the offset correction data when the imaging instruction unit 20 gives an imaging instruction in a time interval from acquisition of a dark image to renewal of offset correction data, i.e., during renewal of the offset correction data and when the timing of renewal of the offset correction data falls during the progress of radiographic imaging or processing of radiographic image data. In other words, it is preferable that taking a radiographic image takes precedence over renewal of offset correction data.

According to such a scheme, a radiologist or a medical doctor and even an examinee H need not be kept waiting for imaging or diagnosis because of the renewal of offset correction data, permitting a stress-free, efficient diagnosis using the imaging system 10.

While said given time interval for renewing the offset correction data is not limited specifically and may be set as appropriate according to, for example, the installation environments of the imaging system 10 and the image quality required, it is preferably 10 minutes to 30 minutes. The threshold of the temperature variation of the FPD 32 for renewing the offset correction data is also not limited specifically and may be set as appropriate according to, for example, the properties of the FPD 32 and the image quality required. It is preferably 5° C. to 10° C.

The time interval and the temperature variation for renewing the offset correction data set to the above ranges are preferable because these ranges permit offset correction to be achieved with a higher accuracy and hold the in-plane image variation to a minimum.

Further, in the first embodiment, the timing for renewing the offset correction data may be determined by factors not limited to the given time interval and the temperature variation of the FPD 32 exceeding a given threshold. For example, renewal of the offset correction data may be made only according to a given time interval, or renewal of the offset correction data may be made only according to the temperature variation of the FPD 32 exceeding a given threshold.

Further, the timing for renewing the offset correction data may be determined in other manners than the above. For example, renewal may be made at one, or two or more combined, of various renewal timings such as a given time of day such as 10 o'clock, 11 o'clock, 13 o'clock, 14 o'clock, and so forth; the end of each recess or pause; when a given length of time has elapsed after radiographic imaging (irradiation); and the like.

The residual image corrector 44 performs residual image correction on an offset-corrected radiographic image supplied from the offset corrector 40. The residual image corrector 44 supplies a residual image-corrected radiographic image to the output unit 18 illustrated in FIG. 1 for the next step.

After the immediately preceding image data has been read out, there remains inside the FPD 32 an electric charge corresponding to the image data, and the residual electric charge is superimposed upon the next image as a residual image from the immediately preceding imaging, which adversely affects the image quality. The residual image corrector 44 performs residual image correction on a radiographic image to prevent occurrence of adverse effects caused by the residual image from the immediately preceding imaging i.e., image deterioration.

In the imaging system 10, the residual image corrector 44 stores the dark image acquired from the FPD 32 as residual image data at a timing that may be preset as appropriate such as when a given time has elapsed after radiographic imaging (irradiation) and subtracts residual image data from the radiographic image to perform residual image correction on the radiographic image.

In the first embodiment, the residual image correction may be performed by any of known methods used with radiographic imaging systems as well as the above method.

When radiographic imaging is performed some time after acquisition of a residual image, a difference arises between the residual image in the FPD 32 as it is at the time of imaging and the stored residual image data, because, as described later in detail, the residual image in the FPD 32 decreases over time. This will make appropriate residual image correction impossible. Therefore, it is preferable to perform residual image amount correction such that residual image data is corrected according to the elapsed time from acquisition of residual data to radiographic imaging.

The output unit 18 outputs the image-processed radiographic image supplied from the image processor 16. The output unit 18 comprises, for example, a monitor for displaying a radiographic image on the screen, a printer for printing a radiographic image, and a memory for storing radiographic image data.

The imaging instruction unit 20 sets an imaging menu, imaging conditions, and the like. and gives instructions for imaging of the subject H. The imaging instruction unit 20 comprises an entry key for setting an imaging menu and imaging conditions and instruction means for giving imaging instructions.

The first embodiment uses a two-step imaging button as imaging instruction means. When the imaging button is depressed to its first step (depressed halfway), the system stands by for imaging; when the imaging button is depressed to its second step (fully depressed), an imaging starts. The imaging instruction unit 20 outputs to the controller 22 instruction signals each representing states where the imaging button is not depressed, the imaging button is depressed to the first step, and the imaging button is depressed to the second step and imaging information such as imaging conditions.

The controller 22 controls the operations of the individual components of the imaging system 10 according to the imaging instruction signal supplied from the imaging instruction unit 20.

The controller 22 controls the imaging unit 12 so that imaging is effected, for example, with a preset imaging menu and preset imaging conditions. Further, the controller 22 controls the radiographic data processor 14 so that a dark image is read out from the radiation detector 32 at a preset timing to renew (produce) offset correction data used for offset correction. More specifically, in the imaging system 10, a dark image is acquired through the radiographic data processor 14 to renew offset correction data at given intervals and when the temperature of the FPD 34 measured by the temperature measuring means 34 has undergone a variation exceeding a given threshold. Further, the controller 22 controls the image processor 16 so that given image processing is performed on a radiographic image as taken (radiographic image data) and a dark image acquired from the radiation detector.

Now, the operations of radiographic imaging achieved by the imaging system 10 according to the first embodiment will be described referring to FIGS. 1 and 2.

The radiographic imaging by the first embodiment of the imaging system 10 may be performed in the same manner as by known radiographic imaging systems.

To be more specific, when the imaging instruction unit 20 gives an imaging instruction through the controller 22, the radiation source 26 irradiates the subject H, and the radiation that has penetrated the subject H is detected and converted into an electric signal by the FPD 32, whereupon a radiographic image is produced from the electric signal thus obtained by conversion. The radiographic data processor 14 reads out the produced radiographic image and performs given data processing such as analog-to-digital conversion on the read-out radiographic image, whereupon the image acquirer 36 acquires and supplies the data-processed radiographic image to the image processor 16. In the image processor 16, the offset correction means 46 uses offset correction data that is renewed immediately before radiographic imaging to perform offset correction on the radiographic image and supplies the offset-corrected image to the residual image corrector 44. The residual image corrector 44 uses residual image data to perform residual image correction on the offset-corrected radiographic image and supplies the residual image-corrected radiographic image to the output unit 18. In the output unit 18, the acquired radiographic image is displayed on the monitor, printed by the printer and/or stored in the memory.

Where the conventional radiographic imaging system renews the offset correction data at a preset timing, appropriate offset correction data cannot be produced in a case where the offset correction data is renewed when there still remains a residual image from the preceding radiographic imaging that was effected with a great dose of radiation. When such offset correction data is used, appropriate offset correction cannot be achieved, and the image quality of the radiographic image deteriorates.

In contrast, according to the first embodiment, a dark image is acquired at a given timing, and the dark image is judged for the presence and absence of a residual image, renewing the offset correction data in the absence of residual image. Thus, the offset correction data is free from the effects of the residual image, making it possible to perform an appropriate offset correction and obtain a high quality radiographic image.

Second Embodiment

According to the first embodiment, when the dark image acquired for offset correction data renewal contains a residual image, the dark image containing a residual image is removed. However, such a dark image containing a residual image may be used to produce residual image data for residual image correction.

Figure 4:
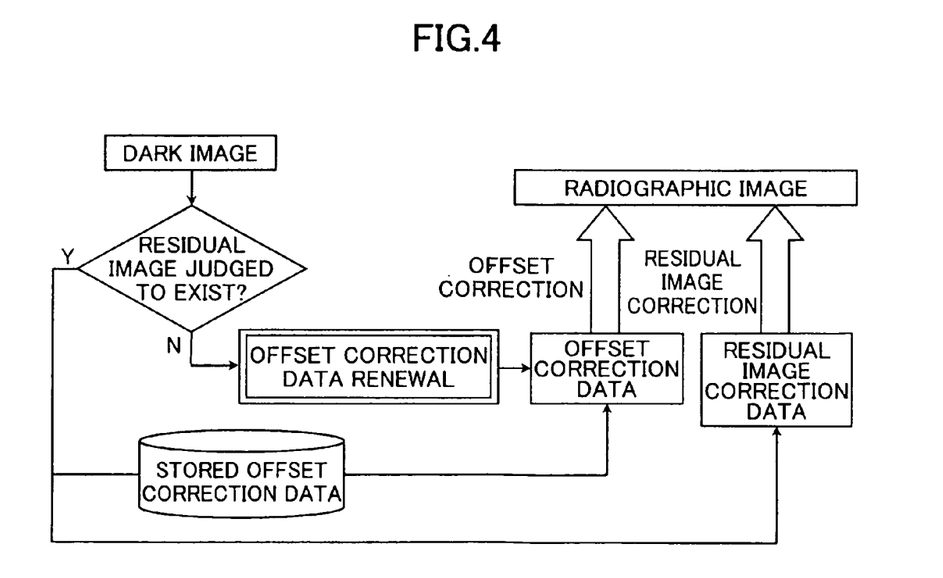
FIG. 4 is a view for explaining operations of offset correction data renewal in a second embodiment.

FIG. 4 illustrates the operations of offset correction data renewal in the second embodiment.

As in the first embodiment, a dark image is supplied to the correction data renewal means 50 at given intervals and at an offset correction data renewal timing in which the FPD 32 has undergone a variation in temperature exceeding a given threshold.

The dark image is judged by the residual image judgment unit 42 for the presence and absence of a residual image.

When the dark image is judged to contain no residual image (N), the correction data renewal means 50 uses this dark image to produces/renews offset correction data, which is used for offset correction until the next renewal is made.

In contrast, when the residual image judgment unit 42 judges that the dark image contains a residual image (Y), the offset correction data is not renewed as illustrated in FIG. 4, and this dark image containing a residual image is supplied to the residual image corrector 44 as a dark image for producing a residual image data used for residual image correction. The residual image corrector 44 uses this dark image to produce a residual image data used for residual image correction thereby to renew the residual image data.

Accordingly, the residual image corrector 44 uses the residual image data produced from the dark image acquired for offset correction data renewal to perform residual image correction until it renews the next residual image data.

In the first and the second embodiments described above, the dark image acquired for offset correction data renewal is judged for the presence and absence of a residual image, and the offset correction data is renewed only when no residual image is found.

Third Embodiment

In the third embodiment of the invention, the offset correction data is renewed basically at given time intervals and at a given timing such as when the FPD 32 has undergone a variation in temperature exceeding a given threshold as in the first and second embodiments. When radiographic imaging (irradiation) has been performed with a dose of radiation exceeding a threshold, however, no offset correction data renewal is made until a given time period has elapsed after that radiographic imaging.

As in the first and second embodiments, appropriate offset correction data renewal is impossible when a dark image acquired for offset correction data renewal contains a residual image.

Figure 5:
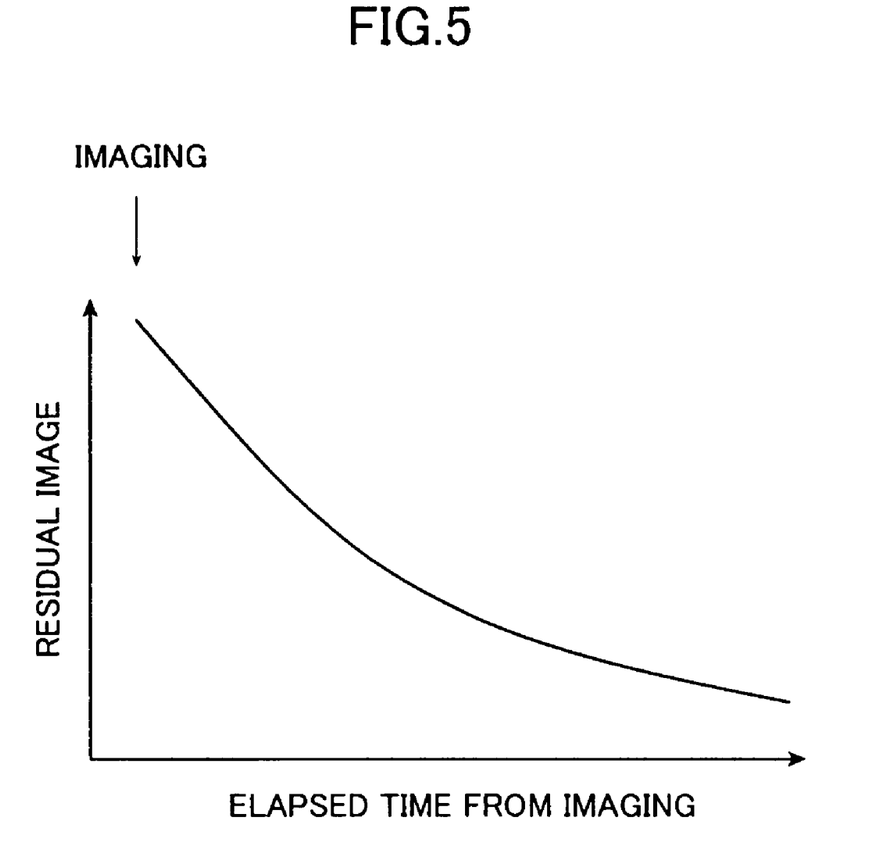
FIG. 5 is a graph illustrating a relationship between the time elapsed from when an image is taken and the amount of residual image.

The amount of the residual image decreases over time after radiographic imaging, as schematically illustrated in FIG. 5. Further, the dose of radiation used for radiographic imaging and the length of time needed for the residual image to have ceased affecting the dark image can be known by conducting experiments or simulations.

In the third embodiment, preset is a threshold of radiation dose over which irradiation will cause non-disregardable residual image to remain. Further, it is a prerequisite to know in advance the time it will take for a residual image to have decreased to such an extent that the residual image ceases affecting the dark image used to produce offset correction data after performing of radiographic imaging with a dose of radiation exceeding that threshold. The time will be referred to below as "residual image fading time".

On that basis, the offset correction data is renewed at said given timing such as at given time intervals. And, when radiographic imaging has been performed with a dose of radiation exceeding the threshold, renewal of the offset correction data is temporally suspended, and resumed at said given timing after the residual image fading time has elapsed. In other words, the offset correction data is not renewed until the residual image fading time has elapsed because a dark image for offset correction data renewal acquired in such a time interval necessarily contains a residual image and therefore processing performed based on that data is useless.

Figure 6:
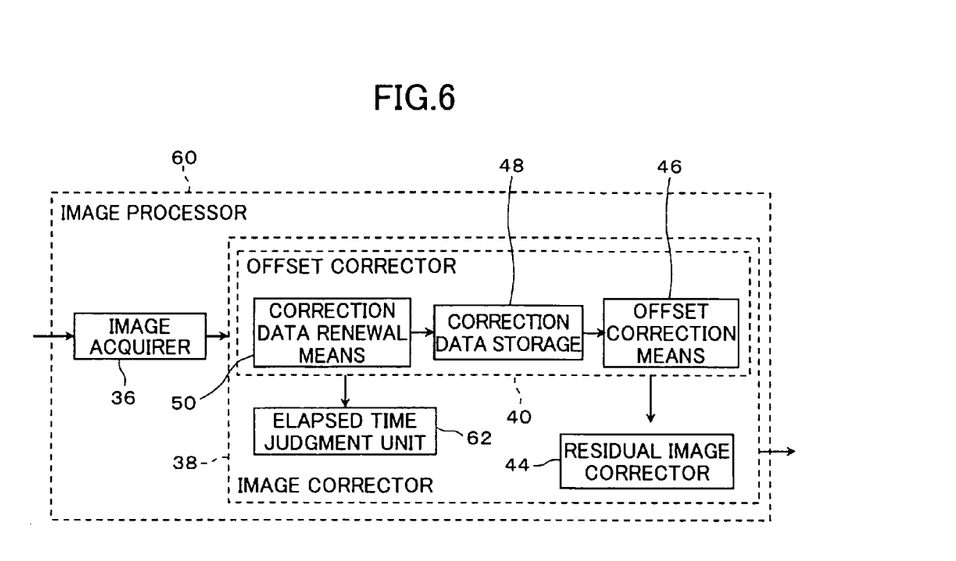
FIG. 6 is a block diagram illustrating a configuration of the image processor in a third embodiment.

FIG. 6 is a block diagram illustrating a configuration of an image processor 60 in the third embodiment of the radiographic imaging system that performs such offset correction data renewal.

In the third embodiment of the radiographic imaging system, the image processor 60 is provided instead of the image processor 16 in the imaging system 10 illustrated in FIG. 1.

The image processor 60 has the same configuration as the image processor 16 except that the former has an elapsed time judgment unit 62 in place of the residual image judgment unit 42. Thus, like components are given like reference characters, focusing upon the components not shared between the two in the description to follow.

The elapsed time judgment unit 62 determines whether or not said residual image fading time has elapsed after radiographic imaging is performed with a dose of radiation exceeding a given threshold.

Thus, the elapsed time judgment unit 62 has a preset residual image fading time stored therein. The elapsed time judgment unit 62 is supplied with information that radiographic imaging has been performed with a dose of radiation exceeding a threshold and information that the radiographic data processor 14 has acquired a dark image for offset correction data renewal. The elapsed time judgment unit 62 judges by using the residual image fading time and the above information whether the offset correction data should be renewed or not.

The threshold of the radiation dose may be determined according to the properties of the FPD 32 such as predisposition to retain a residual image.

As described earlier, the residual image fading time may be determined as appropriate according to, for example, the required image quality of the radiographic image and the required offset correction accuracy by conducting experiments or simulations. For example, the residual image fading time may be a time it takes for a dark image reproduced as a visible image to have decreased to a radiodensity beyond visual recognition. Alternatively, the residual image fading time may be a time it takes for the radiodensity of a dark image reproduced as a visible image to have decreased to below a threshold determined as appropriate according to the required offset correction accuracy.

Figure 7:
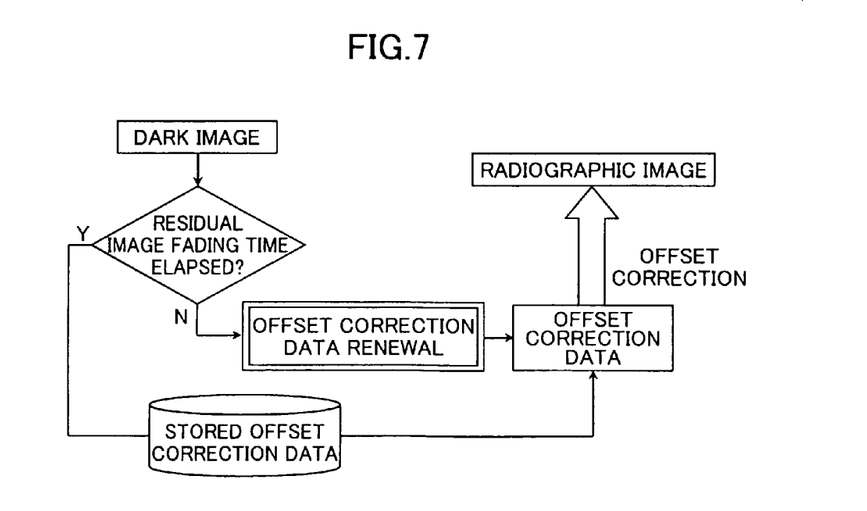
FIG. 7 is a view for explaining the operations of offset correction data renewal in an elapsed time judgment unit in the third embodiment.

Now, the offset correction data renewal processing performed by the image processor 60 and the elapsed time judgment unit 62 will be described referring to FIG. 7.

As in the first and second embodiments, the radiographic data processor 14 acquires a dark image for renewing offset correction data from the FPD 32 at given intervals or when the FPD 32 has undergone a variation in temperature exceeding a given threshold in a time interval from the startup of the system until the system is switched off, and supplies the acquired dark image to the correction data renewal means 50.

The information on the acquisition of the dark image is supplied to the elapsed time judgment unit 62. When the radiographic imaging system has performed radiographic imaging with a dose of radiation exceeding a given threshold, the information thereon is also supplied to the elapsed time judgment unit 62. A determination whether or not radiographic imaging has been performed with a dose of radiation exceeding a threshold may be made by detecting the tube voltage of the radiation source 26, the irradiation time, radiation intensity detection result yielded by sensors provided in the imaging table 28, an output intensity from the FPD (radiodensity) as measured outside the area thereof where the subject H lies, and the like using an appropriate conventional method.

The elapsed time judgment unit 62 judges whether or not a dark image is acquired from the FPD 32 after the residual image fading time has elapsed from radiographic imaging using a dose of radiation exceeding a given threshold.

When the judgment is made in which a dark image is acquired from the FPD 32 after the residual image fading time has elapsed (Y), the elapsed time judgment unit 62 gives a renewal instruction to the correction data renewal means 50, which renews the offset correction data using the supplied dark image.

On the other hand, when the acquisition of a dark image from the FPD 32 precedes the lapse of the residual image fading time (N), the elapsed time judgment unit 62 gives an instruction that no renewal be made to the correction data renewal means 50. Therefore, the offset correction data is not renewed. In this case, the offset correction data may be treated as in the first and second embodiments.

More specifically, when radiographic imaging has been performed with a dose of radiation exceeding a threshold in the third embodiment, no offset correction data renewal is made until the residual image fading time has elapsed. This permits appropriate offset correction data renewal using an appropriate dark image free from a residual image, making it possible to perform a consistently appropriate offset correction and obtain a high quality radiographic image.

In the third embodiment, the dark image for offset correction data renewal is acquired at a given timing for the elapsed time judgment unit 62 to determine whether or not the residual image fading time has elapsed. The invention is, however, not limited this way.

An example of such an alternative is not to acquire the dark image for offset correction data renewal from the FPD 32 until the residual image fading time has elapsed when radiographic imaging has been performed with a dose of radiation exceeding a threshold.

In the third embodiment, it is preferable that the residual image fading time is preset stepwise according to the dose of radiation exceeding a threshold (naturally, the residual image fading time should increase with the dose of radiation used).

To eliminate the adverse effects on the offset correction data more consistently and reliably, the residual image fading time would need to be set according to an assumed maximum dose of radiation. Such an approach, however, would delay the renewal of the offset correction data by as long as the residual image fading time corresponding to the maximum dose of radiation even when the radiographic imaging has been performed with a dose of radiation that only slightly exceeds a threshold.

In contrast, setting a residual image fading time set stepwise according to the dose of radiation exceeding a threshold avoids making the residual image fading time unnecessarily long after a radiographic imaging is performed with a dose of radiation exceeding a threshold and permits efficient, appropriate renewal of the offset correction data.

The radiographic imaging system of the invention may be adapted to renew the offset correction data according to both the first and the third embodiments.

More specifically, the dark image is acquired at a given timing as described above such as at given time intervals and when the FPD 32 has undergone a variation in temperature exceeding a given threshold, and judgment is made thereon as to the presence or absence of a residual image, whereupon offset correction data is renewed when the dark image is judged to have no residual image and no offset correction data renewal is made when the dark image is judged to have a residual image. According to an additional option, when radiographic imaging has been performed with a dose of radiation exceeding a preset threshold, the offset correction data is not renewed (or the dark image for renewal is not acquired) until a preset residual image fading time has elapsed regardless of the judgment result as to the presence/absence of the dark image, and the offset correction data renewal including the residual image judgment is resumed at said given timing after the lapse of the residual image fading time.

While the radiographic imaging system of the invention has been described in detail, the above embodiment is only illustrative of the invention, and it is to be understood that various changes and modifications may be made without departing from the spirit of the invention.

What is claimed is:

1. A radiographic imaging system comprising:
   a radiation source for irradiating a subject with radiation,
   a radiation detector for detecting radiation that has penetrated the subject to acquire a radiographic image,
   a storage for storing offset correction data,
   offset correction means for performing offset correction on a radiographic image acquired by the radiation detector using the offset correction data in the storage,
   dark image acquisition means for acquiring a dark image with the radiation detector at a given timing in the absence of radiation emitted from the radiation source,
   residual image judgment means for judging whether or not a dark image acquired by the dark image acquisition means contains a residual image resulting from an immediately preceding irradiation, and
   offset correction data renewal means for producing offset correction data based upon the dark image and storing the offset correction data in the storage for renewal when the residual image judgment means judges the dark image to contain no residual image, and producing no offset correction data when the residual image judgment means judges the dark image to contain a residual image.

2. The radiographic imaging system according to claim 1, further comprising residual image correction means for correcting the residual image of the radiographic image,
   wherein, when the residual image judgment means judges the dark image to contain a residual image, the residual image correction means uses the dark image to correct the residual image of the radiographic image.

3. The radiographic imaging system according to claim 1, wherein, when the radiation source has performed irradiation with a dose of radiation exceeding a given threshold, the offset correction data renewal means does not renew the offset correction data until a given time period has elapsed from the irradiation.

4. The radiographic imaging system according to claim 3, wherein the given time period from the irradiation is determined according to a dose of radiation with which the irradiation has been performed.

5. The radiographic imaging system according to claim 1, wherein the dark image acquisition means acquires the dark image at given time intervals.

6. The radiographic imaging system according to claim 1, further comprising temperature detection means for detecting a temperature of the radiation detector,
wherein when a judgment is made that the radiation detector has undergone a variation in temperature exceeding a given threshold based upon a temperature detected by the temperature detection means, the dark image acquisition means acquires the dark image regardless of the given timing.

7. A radiographic imaging system comprising:
a radiation source for irradiating a subject with radiation,
a radiation detector for detecting radiation that has penetrated the subject to acquire a radiographic image,
a storage for storing offset correction data,
offset correction means for performing offset correction on the radiographic image acquired by the radiation detector using the offset correction data in the storage,
dark image acquisition means for acquiring a dark image with the radiation detector at a given timing in the absence of radiation emitted from the radiation source,
elapsed time judgment means for judging whether or not a given time period has elapsed after the radiation source has performed irradiation with a dose of radiation exceeding a given threshold, and
offset correction data renewal means for producing offset correction data based upon the dark image and storing the offset correction data in the storage for renewal when the elapsed time judgment means judges that the given time period has elapsed, and producing no offset correction data when the elapsed time judgment means judges that the given time period has not elapsed.

8. The radiographic imaging system according to claim 7, wherein the given time period from the irradiation is determined according to the dose of radiation with which the irradiation has been performed.

9. The radiographic imaging system according to claim 7, wherein the dark image acquisition means acquires the dark image at given time intervals.

10. The radiographic imaging system according to claim 7, further comprising temperature detection means for detecting a temperature of the radiation detector,
wherein when a judgment is made that the radiation detector has undergone a variation in temperature exceeding a given threshold based upon a temperature detected by the temperature detection means, the dark image acquisition means acquires the dark image regardless of the given timing.

* * * * *